United States Patent [19]

Swim et al.

[11] Plant 4,707

[45] May 5, 1981

[54] ROSE PLANT

[75] Inventors: Herbert C. Swim, Ontario; Arnold W. Ellis, Garden Grove, both of Calif.

[73] Assignee: Armstrong Nurseries, Inc., Ontario, Calif.

[21] Appl. No.: 106,545

[22] Filed: Dec. 26, 1979

[51] Int. Cl.[3] ..... A01H 5/00

[52] U.S. Cl. ..... Plt./18

[58] Field of Search ..... Plt./18

*Primary Examiner*—James R. Feyrer

*Attorney, Agent, or Firm*—William H. Elliott, Jr.; Andrew R. Klein

[57] ABSTRACT

A new variety of hybrid tea rose, being a tender seedling of the tall bush type, well adapted for greenhouse cultivation. The plant is of upright-bushy habit, moderately branched and moderately vigorous in growth. Blooms are borne singly, and have a uniform all-over pink coloration which lightens with maturity to a pink color slightly less deep than at first opening. There is a moderate tea fragrance, with a somewhat spicy cast.

1 Drawing Figure

This invention relates to a new class of hybrid tea rose. The plant is a tender seedling of the tall bush type, cultivated in a greenhouse primarily for cut flowers. It was propagated by Herbert C. Swim and Arnold W. Ellis in Ontario, Calif., having as its seed parent "White Satin", U.S. Plant Pat. No. 2,648, and, as its pollen parent, "Bewitched", U.S. Plant Pat. No.2,755. It holds its distinguishing characteristics through succeeding propagations by budding.

The new variety bears its flowers singly, on normal to strong, medium-length to long stems. The plant blooms freely in the greenhouse, and continuously during the growing season. It has a moderate tea to spicy fragrance.

This new cultivar may be distinguished from its seed parent, White Satin, by the following characteristics:

White Satin bears large white flowers with a greenish yellow center, whereas the new rose bears large pink flowers of relatively uniform coloration.

White Satin has a notably larger number of petals, from sixty to eighty, than the new cultivar, which has from thirty-five to forty-five petals.

This new cultivar may be distinguished from its pollen parent, Bewitched, by the following characteristics:

The foliage of Bewitched has a notably more glossy finish than the foliage of the new rose.

Bewitched normally bears flowers with a 5-inch diameter, whereas the new cultivar bears significantly smaller flowers, ranging in size from 3½ to 4½ inches.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is average length to long, and average caliper, erect and stiff. It is almost smooth with a few stipitate glands. The color ranges from Moderate Olive Green, 5GY4/3, at the base to Dark Greenish Yellow, 7.5Y6/7, near the bud.

Before the calyx breaks, the bud is medium to large in size, and medium-length to long, pointed and ovoid in form, with light tomentum on the surface of the bud. There are usually slender foliaceous parts extending beyond the tip of the bud equal to one-fourth or more of its length.

As the calyx breaks, the color is between Strong Pink, 10RP7/8, and Strong Pink, 2.5R7/8.

The inner surface of the sepals has a fine tomentum; margins are lined with stipitate glands.

As the first petal opens, the bud is average in size, medium-length to long, pointed and ovoid in form. The color on the outside of the petal is Brilliant Greenish Yellow, 10Y9/9, in a small zone at the basal attachment point, while the remainder of the petal suffuses to near Strong Purplish Red, 10RP5/12. The inside surface of the petal is Brilliant Greenish Yellow, 10Y9/9, in a slightly larger zone at the basal attachment point, while the majority of the petal is between Deep Pink, 10RP6/12, and Strong Purplish Red, 10RP5/12. The bud opens up well and is not prevented from opening by hot, wet, or dry weather.

BLOOM

The size of the bloom when fully open is average to large, ranging from 3½ to 4½ inches. The petalage is double, with from 35 to 45 petals, plus from 5 to 10 petaloids, arranged regularly. The bloom is full and high centered at first, becoming open to cupped. At first the petals remain somewhat tightly cupped, with tips rolled outward, becoming later at maturity more flat, with tips rolled outward.

The petals are of medium thickness and moderately soft, with the inside slightly satiny and the outside slightly shiny. The outside petals are round to broadly obovate. The intermediate petals are round and the inside petals broadly obovate. The colors may be modified by being dotted, shaded and/or washed or tinted with other colors.

The paragraphs immediately following describe the color values observed in a flower newly opened in the month of June. The plant had been grown in a greenhouse, in Ontario, Calif.

The outer surface of the outside petal showed a basal attachment zone of near Brilliant Greenish Yellow, 7.5Y9/8, with the majority of the petal being between Strong Pink, 10RP7/8, and Strong Purplish Pink, 7.5RP7/10. The inner surface of the outside petal showed a basal attachment zone of near Brilliant Greenish Yellow, 10Y9/9, with the majority of the petal corresponding to the color of the outer surface.

The outer surface of the intermediate petals and the inner petals were the same as the outer surface of the outside petal described above. The inner surfaces of both the intermediate and the inner petals showed a basal attachment point of near Brilliant Greenish Yellow, 10Y9/9, with the majority of the petal being near Deep Pink, 10RP6/12.

The paragraph immediately following describes color values observed in a bloom which had been open for three days, in the greenhouse, in the month of June. The plant had been grown in the greenhouse in Ontario, Calif.

The outer surface of all petals, outside and inside, showed a basal attachment zone of near Brilliant Greenish Yellow, 10Y9/9, with the majority of the petal near Strong Purplish Pink, 7.5RP7/10.

The general color effect of the newly opened flower is between Strong Purplish Pink, 7.5RP7/10, and Strong Pink, 10RP7/8. The bloom after being three days open gives a general color effect which is between Light Purplish Pink, 7.5RP8/5, and Strong Purplish Pink, 7.5RP7/10. The petals persist, fading to near Pale Purplish Pink, 7.5RP9/2, and are not particularly affected by cold, hot, wet or dry weather.

Cut roses grown in the greenhouse and kept at living-room temperatures will last from 3 to 5 days in the month of June.

REPRODUCTIVE ORGANS

The stamens are from average to many in number, arranged regularly about the pistils, a few being tucked in the calyx.

The filaments are from short to medium-length. The color is near Strong Orange, 2.5YR6/12. Most are with anthers.

The anthers are medium size to large, all opening approximately at once, the immature being near Strong Orange Yellow, 10YR7/10, the mature anthers being near Strong Yellowish Brown, 7.5YR5/7.

Pollen is abundant and between white and Brilliant Greenish Yellow, 7.5Y9/8, in color.

There are many pistils, being approximately 60 in number.

The styles are moderately uneven, from short to average length, thin to average caliper and loosely bunched. The color is near Brilliant Greenish Yellow, 7.5Y9/8.

The stigma is near Dark Reddish Orange, 7.5R4/11, in color.

The ovaries are usually enclosed in the calyx, but some protrude therefrom.

The hips are of average length, ovoid, and smooth, with thick fleshy walls. Their color is near Strong Yellow Green, 5GY6/8, with a slight gray bloom.

The sepals are permanent, medium-length to long, and spear-shaped. The color on both the inside and the outside is near Strong Yellow Green, 5GY6/8, with a fine tomentum on the inside.

Seeds are average in number, being from 5 to 15, and medium size to large.

FOLIAGE

The compound leaves usually comprise from three to five leaflets. There is a normal amount of such leaves, which are large, somewhat leathery and semi-glossy. The leaflets are ovate, with apex acute to mucronate, and with round base. The margin is simply serrate, reflexing toward the underside.

The mature foliage displays upon its upper surface a color which is between Dark Yellowish Green, 10GY4/5, and Moderate Olive Green, 7.5GY4/4. The under surface is near Moderate Yellow Green, 7.5GY5/7, but washed heavily with gray.

The young foliage on its upper surface is between Strong Red, 5R4/12, and Dark Red, 5R3/7, in color. On its under surface, it is between Dark Red, 5R3/7, and Dark Red, 2.5R3/7.

The rachis is average size to heavy, grooved on its upper side, with a few stipitate glands on the edges, the under side being moderately smooth.

The stipules are medium-length to long, medium-width, with moderately long points, turning out at an angle of less than 45°.

The plant displays a more than average resistance to mildew compared to other commercial varieties grown in the locality named under comparable conditions.

GROWTH

The plant is of upright-bushy habit, moderately branched. It displays a moderately vigorous growth. The canes are of medium to heavy caliper.

The main stems are near Light Olive, 10Y5/5, in color. They bear few large prickles which are medium-length to long, almost straight, with medium-length, moderately narrow base. The color is between gray and Moderate Brown, 7.5YR4/5. There are no small prickles and no hairs.

The branches are a color between Moderate Yellow Green, 2.5GY5/5, and Moderate Olive Green, 2.5GY4/3. They bear few large prickles, which are medium-length to long, almost straight, with medium-length, moderately narrow base. The color is near Brilliant Yellow, 5Y9/9. There are no small prickles and no hairs.

New shoots are near Moderate Reddish Brown, 2.5YR3/3, in color. They bear few large prickles, which are medium-length, almost straight, with medium-length narrow base. The color is between Dark Red, 2.5R3/7, and Dark Red, 5R3/7. There are no small prickles and no hairs.

We claim:

1. A new and distinct variety of rose plant of the hybrid tea class, substantially as herein shown and described, being particularly characterized in its tendency to carry its blooms singly on normal to strong medium-length to long stems, the blooms being generally from $3\frac{1}{2}$ to $4\frac{1}{2}$ inches across, and having a relatively uniform pink coloration throughout, with from about 35 to 45 petals.

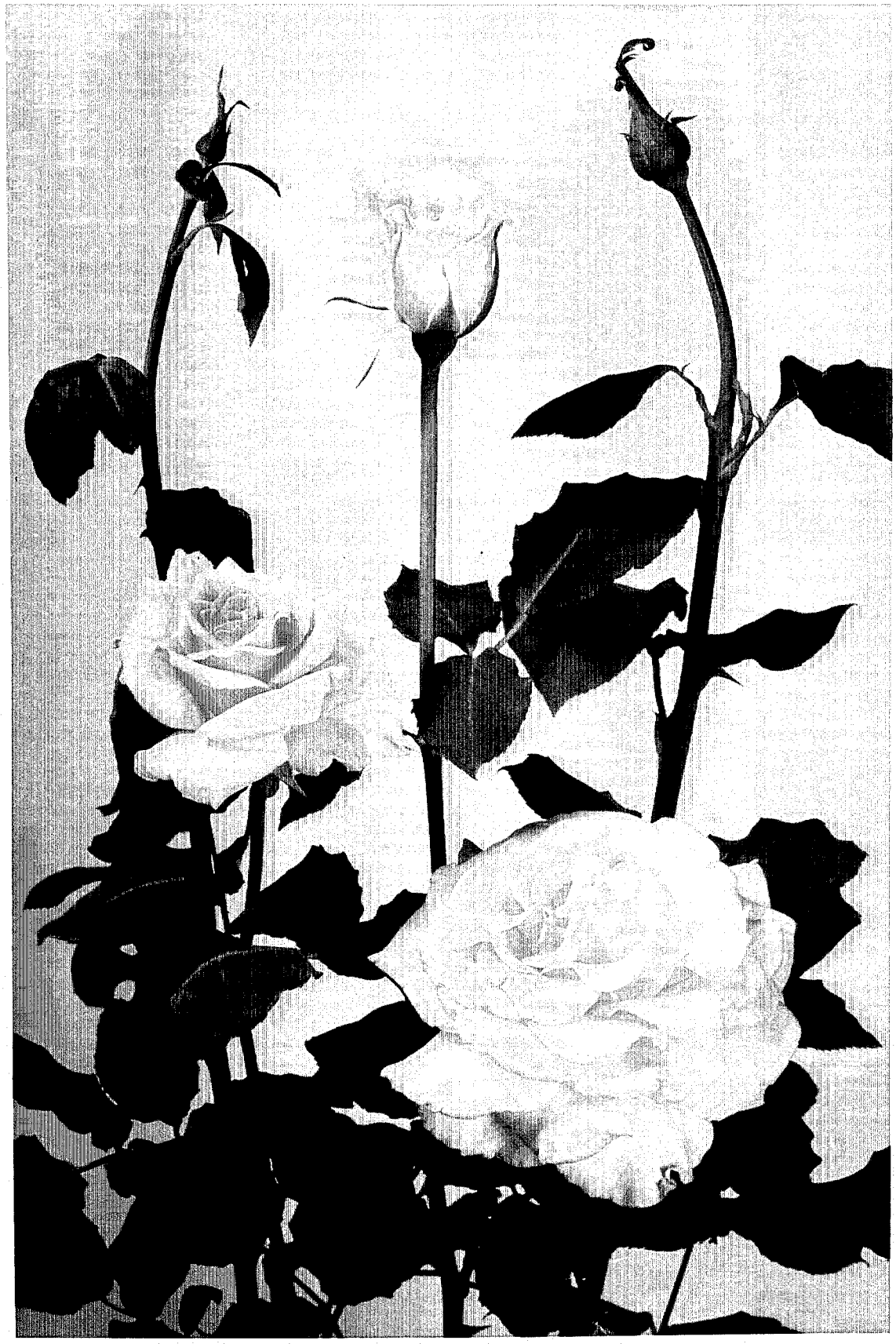

* * * * *